(12) United States Patent
Mousa et al.

(10) Patent No.: US 8,202,736 B2
(45) Date of Patent: Jun. 19, 2012

(54) METHOD OF HORMONE EXTRACTION USING DIGITAL MICROFLUIDICS

(75) Inventors: Noha Ahmed Mousa, Toronto (CA); Mais J. Jebrail, Richmond Hill (CA); Mohamed Omar Abdelgawad, Toronto (CA); Aaron R. Wheeler, Toronto (CA); Robert Fredric Joseph Casper, Toronto (CA)

(73) Assignee: The Governing Council of the University of Toronto, Toronto, ON (CA)

( * ) Notice: Subject to any disclaimer, the term of this patent is extended or adjusted under 35 U.S.C. 154(b) by 584 days.

(21) Appl. No.: 12/379,704

(22) Filed: Feb. 26, 2009

(65) Prior Publication Data

US 2010/0213074 A1 Aug. 26, 2010

(51) Int. Cl.
G01N 33/536 (2006.01)
(52) U.S. Cl. ........................................................ 436/536
(58) Field of Classification Search .................... None
See application file for complete search history.

(56) References Cited

U.S. PATENT DOCUMENTS

| | | | |
|---|---|---|---|
| 4,569,575 A | 2/1986 | Le Pesant et al. | |
| 4,636,785 A | 1/1987 | Le Pesant | |
| 4,818,052 A | 4/1989 | Le Pesant et al. | |
| 5,486,337 A | 1/1996 | Ohkawa | |
| 6,352,838 B1 | 3/2002 | Krulevitch et al. | |
| 6,565,727 B1 | 5/2003 | Shenderov | |
| 6,773,566 B2 | 8/2004 | Shenderov | |
| 6,911,132 B2 | 6/2005 | Pamula et al. | |
| 6,989,234 B2 | 1/2006 | Kolar et al. | |
| 7,147,763 B2 | 12/2006 | Elrod et al. | |
| 7,163,612 B2 | 1/2007 | Sterling et al. | |
| 7,214,302 B1 | 5/2007 | Reihs et al. | |
| 7,255,780 B2 | 8/2007 | Shendervo | |
| 7,328,979 B2 | 2/2008 | Decre et al. | |
| 7,329,545 B2 | 2/2008 | Pamula et al. | |
| 2004/0171169 A1 | 9/2004 | Kallury et al. | |
| 2004/0211659 A1 | 10/2004 | Velev | |
| 2005/0115836 A1 | 6/2005 | Reihs | |
| 2005/0148091 A1 | 7/2005 | Kitaguchi et al. | |
| 2005/0191759 A1 | 9/2005 | Pedersen-Bjergaard et al. | |
| 2007/0023292 A1 | 2/2007 | Kim et al. | |
| 2007/0148763 A1 | 6/2007 | Huh et al. | |
| 2007/0242111 A1 | 10/2007 | Pamula et al. | |
| 2008/0044914 A1 | 2/2008 | Pamula et al. | |
| 2008/0156983 A1 | 7/2008 | Fourrier et al. | |
| 2008/0185339 A1* | 8/2008 | Delapierre et al. | 210/634 |
| 2009/0203063 A1 | 8/2009 | Wheeler et al. | |
| 2010/0081578 A1 | 4/2010 | Wheeler et al. | |
| 2010/0087633 A1 | 4/2010 | Wheeler et al. | |
| 2010/0213074 A1 | 8/2010 | Mousa et al. | |
| 2010/0311599 A1 | 12/2010 | Wheeler et al. | |

FOREIGN PATENT DOCUMENTS

| | | |
|---|---|---|
| WO | 2007120241 A2 | 10/2007 |
| WO | 2007136386 A1 | 11/2007 |
| WO | 2008051310 A3 | 5/2008 |
| WO | 2010040227 | 4/2010 |

OTHER PUBLICATIONS

Chatterjee et al., "Droplet-based microfluidics with nonaqueous solvents and solutions", Lap Chip, 2006, vol. 6, pp. 199-206.
Jebrail et al., "Digital Microfluidic Method for Protein Extraction by Precipitation", Analytical Chemistry, Jan. 1, 2009, vol. 81, No. 1, pp. 330-335.
Moon et al., "An integrated digital microfluidic chip for multiplexed proteomic sample preparation and analysis by MALDI-MS", Lab Chip, 2006, vol. 6, pp. 1213-1219.
Shih-Kang Fan "Cross-scale electric manipulations of cells and droplets by frequency modulated dielectrophoresis and electrowetting" The Royal Society of Chemistry (2008), Lab Chip vol. 8, pp. 1325-1331.
Ting-Hsuan Chen. "Selective Wettability Assisted Nanoliter Sample Generation Via Electrowetting-Based Transportation," Proceedings of the Fifth International Conference on Nanochannels, Microchannels and Minichannels (ICNMM) (Jun. 18-20, 2007).
Hongmei Yu. "A plate reader-compatible microchannel array for cell biology assays," The Royal Society of Chemistry (2007) Lab Chip vol. 7, pp. 386-391.
Marc A. Unger. "Monolithic Microfabricated Valves and Pumps by Multilayer Soft Lithography," Science (2000) vol. 288.
A.S. Verkman, "Drug Discovery in Academia," Am J Physiol Cell Physiol (2004) vol. 286, pp. 465-474.
Jamdl Ei Ali. "Cells on chips," Nature (2006) Insight Review, vol. 442.
Darren R. Link. "Electric Control of Droplets in Microfluidic Devices," Communicatons, Angew Chem. Int (2006) vol. 45 pp. 2556-2560.
Wheeler Aaron A. "Electrowetting-Based Microfluidics for Analysis of Peptides and Proteins by Matrix-Assisted Laser Desorption/Ionization Mass Spectrometry," (Aug. 2004) Anal Chem. vol. 76, No. 16.
Eun Zoo Lee, "Removal of bovine serum albumin using solid-phase extraction with in-situ polymerized stationary phase in a microfluidic device," ScienceDirect, Journal of Chromatography A. (2008) vol. 1187, pp. 11-17.
Hsih Yin Tan, "A lab-on-a-chip for detection of nerve agent sarin in blood," The Royal Society of Chemistry (2008), Lab Chip vol. 8, pp. 885-891.

(Continued)

Primary Examiner — Ann Lam
(74) Attorney, Agent, or Firm — Lynn C. Schumacher; Stephen W. Leonard; Hill & Schumacher (57) ABSTRACT

A method of extracting hormones from a biological sample using digital microfluidic arrays is provided. Biological samples containing hormones are dried on a digital microfluidic array, lysed by a lysing solvent, dried, subsequently dissolved in a polar solvent, and further purified in an extraction step in which droplets are transported through a volume of non-polar solvent. The method disclosed herein provides the distinct advantage of an automated sample preparation method that is capable of extracting hormones from low sample volumes with excellent precision and recovery.

43 Claims, 6 Drawing Sheets

OTHER PUBLICATIONS

Kai-Cheng Chuang. "Direct Handwriting Manipulation of Droplets by Self-Aligned Mirror-EWOD Across A Dielectric Sheet," MEMS (Jan. 2006) pp. 22-26.

Mohamed Abdelgawad. "Low-cost, rapid-prototyping of digital microfluidics devices," Springer, Microfluid Nanofluid (2008) vol. 4, pp. 349-355.

Eric Lebrasseur. "Two-dimensional electrostatic actuation of droplets using a single electrode panel and development of disposable plastic film card," ScienceDirect, Sensors and Actuators (2007) vol. 136, pp. 358-366.

* cited by examiner

METHOD OF HORMONE EXTRACTION USING DIGITAL MICROFLUIDICS

FIELD OF THE INVENTION

The present invention relates to a method of hormone extraction from biological samples using digital microfluidic arrays, and more particularly the present invention provides a method of sex hormone extraction from small volumes of biological samples by digital microfluidic arrays.

BACKGROUND OF THE INVENTION

Hormones are chemical messengers that transport a signal from one cell to another. They play important roles in regulation of physiological activities. The effects of hormones include stimulation or inhibition of growth, regulating metabolism, induction or suppression of programmed cell death, and controlling the reproductive cycle, just to name a few. Thus, there are a wide range of clinical conditions that require frequent monitoring of hormones in biological samples, such as blood or tissue, for proper diagnosis and treatment of physiological disorders associated with the hormones.

For example, sex steroids are steroid hormones which are fundamental for growth and reproduction, and disturbances in their physiological levels can cause a multitude of clinical disorders, including growth retardation, infertility, or hormone-sensitive cancers (e.g., breast, endometrial and prostate cancers) [1-4]. Moreover, exogenous sex steroids have been used for decades as contraceptives, hormone replacements, and fertility and anti-cancer therapies [5-9]. Estrogen is a steroidal sex hormone of fundamental importance for normal human growth, reproduction and in breast cancer development and progression.

Diagnostic assays for the measurement of sex steroids are of central importance to the management of a wide range of clinical conditions and also play a key role in many areas of epidemiological study. Many clinical applications, such as the monitoring of blood levels of estradiol and other hormones in women undergoing treatment for infertility, have spurred the development of highly automated and cost-effective immunoassays.

Unfortunately, modern immunoassays often lack the low limit of detection required for some clinical areas, including monitoring menopausal women, patients on anti-estrogen therapies [10], or children [11-13]. Indeed, these clinical segments often present cases where the required assay dynamic range falls below the practical detection limits of commercial assays. This lack of performance in commercial assays has been demonstrated in studies of multiple automated analyzers, where considerable variability has been observed in results for samples with low concentrations. This failure of modern automated assays for sex steroids to address the clinical requirements in patient segments presenting low concentrations has prompted the Endocrinology Society to issue a statement cautioning against the use of standard assays for low level testosterone measurements. In recent years, a consensus has emerged that mass spectroscopy provides the optimal performance for low level steroid measurement.

Despite the widespread acknowledgement of the utility of mass spectroscopy as a preferred diagnostic tool low level steroid measurements, one of the key problems that limits its practical performance is sample preparation. Assays for steroids in clinical samples often require extensive pre-processing to extract the analytes from the matrix (i.e., unwanted chemical constituents and insoluble tissue debris). This is the case for all tissue samples, whole blood, and plasma and for any samples (including serum) that are to be evaluated by mass spectrometry or indirect immunoassays. Moreover, such processing techniques are known to be especially important for accurate quantification in subjects with low hormone levels. Unfortunately, sample processing techniques for analysis of steroids (including lysis, homogenization, extraction, and resolubilization) are labor-intensive (wasting many hours of laboratory time [14, 15]), and are thus prone to human error. Furthermore, assays often require hundreds of milligrams of tissue [16, 17] or milliliters of blood [18], which is ill-suited for routine clinical testing.

One promising technology for improved sample preparation is digital microfluidics. Digital microfluidics is a new technology in which discrete unit droplets are manipulated in air on the open surface of an array of electrodes by applying voltages to the electrodes [19]. Sample and reagent droplets with volumes of less than one microliter can be moved in multiple and reconfigurable paths defined by the actuation sequence of an array of electrodes. The mechanism for fluid motion depends on a host of factors and may be due to electrowetting or dielectrophoresis. Unlike conventional microfluidics, digital microfluidics enables the transport, mixing, merging and dispensing from reservoirs of single isolated droplets. The technology has been demonstrated for diverse applications including cell based assays, enzyme assays, protein profiling, and polymerase chain reaction [41].

Digital microfluidic arrays are typically made by depositing an array of electrodes onto a first planar surface and subsequently coating the surface with a layer of a hydrophobic insulator such as Teflon-AF. Electrical contact pads are connected to the electrodes, enabling the electrodes to be individually addressed. Sample and reagent reservoirs are incorporated into the array by including electrodes capable of supporting more than one unit droplet of fluid. Unit droplets can be extracted from reservoirs by actuating electrodes adjacent to the reservoir.

In a closed digital microfluidic array, a second planar surface, onto which a single planar electrode is typically deposited and subsequently coated with a layer of a hydrophobic insulator, is placed parallel to the first planar surface, forming a planar air gap. Accordingly, droplets are sandwiched between the two surfaces. Fluid droplets placed on the array elements (i.e. on the insulating layer directly above an array electrode) can be made to move by applying a voltage between an array electrode and the single planar electrode. Alternatively, an open digital microfluidic array can be formed with the first surface alone, where droplets are moved by applying a voltage between neighbouring electrodes.

While digital microfluidic systems have been successfully developed for a wide range of practical uses, the prior art has not provided a method of adapting their use to the efficient extraction of sex steroids or other hormones from biological samples. Thus, there is a need for a fast, economical and reliable method for analysis of hormone extraction and analysis in biological samples using digital microfluidics.

SUMMARY OF THE INVENTION

The present invention provides a method for the extraction of hormones from biological samples using a digital microfluidic array. The hormones can be lipid hormones (for example, steroid hormones, sterol hormones and prostaglandins), amine derived hormones, peptide and protein hormones. The steroid hormones are selected from the group consisting of estrogens, androgens, progestagen, glucocorticoids and mineralocorticoids. According to one embodiment of the invention, the steroid hormone is sex steroid, preferably estrogen or testosterone. Estrogen includes estradiol, estrone, estriol, estrogen metabolites, phytoestrogens, synthetic estrogens (such as equilin, equilenin, ethinyl estradiol) and bioidentical estrogens. Preferably, estrogen is estradio.

The method of the present invention can also be used in a test for synthetic substances, such as anabolic steroids, and therefore useful in a steroid test in athletes.

In one aspect of the invention, there is provided a method of extracting one or more hormones from a volume of biological sample using a digital microfluidic array, including the steps of:

(a) drying said biological sample at a sample reservoir addressable by said array;

(b) adding a volume of lysing solvent to a lysing reservoir addressable by said array and actuating said array to transport said volume of lysing solvent to said sample reservoir, and drying said lysing solvent at said sample reservoir;

(c) adding a volume of polar solvent to a polar solvent reservoir addressable by said array and actuating said electrode array to transport said volume of polar solvent to said sample reservoir, thereby obtaining a solution in which said one or more hormones are dissolved;

(d) actuating said electrode array to transport a droplet of said solution from said sample reservoir to an extraction reservoir containing a volume of non-polar solvent, said non-polar solvent chosen to extract contaminants from said droplet of said solution while maintaining said droplet of said solution as a distinct liquid phase that can be transported by said electrode array relative to said non-polar solvent;

(e) actuating said electrode array to transport said droplet of said solution from said extraction reservoir to an output reservoir; and (f) repeating steps (d) and (e) until said solution has been substantially removed from said sample reservoir, thereby obtaining a volume of purified solution located at said output reservoir.

In a preferred embodiment, step (b) is repeated one or more times to enable optimal sample lysis. In another preferred embodiment, steps (c)-(f) are repeated one or more times to obtain optimal extraction.

The invention further provides a method for measuring the concentration of one or more hormones from a biological sample, comprising the steps of:

(a) purifying said sample according to the aforementioned of extracting one or more hormones from a volume of biological sample using a digital microfluidic array;

(b) performing an assay to measure a concentration of said one or more hormones in said purified solution; and (c) obtaining a concentration of said one or more hormones in said biological sample by multiplying said concentration of said one or more hormones in said purified solution by a suitable correction factor.

In a preferred embodiment of the above method, the assay is an immunoassay and is selected from the group consisting of ELISA, EIA, RIA, lateral flow and flow-through, and Magnetic Immunoassay. In a more preferred embodiment, the assay is mass spectroscopy and is selected from the group consisting of GC/MS, LC/MS, LC/MS/MS, MALDI-MS, MALDI-TOF, DESI-MS and IMS/MS.

The inventive method is compatible with a range of clinical samples, including tissue, blood, serum, urine, plasma, follicular fluid, endometrial fluid, pelvic fluid, semen and cerebrospinal fluid. The tissue can be breast tissue, endometrial tissue, ovarian tissue, vaginal tissue, testicular tissue, prostate tissue, adipose tissue, brain tissue, liver tissue, hair and skin.

The new method is fast and automated, and features a potentially 1000× reduction in required sample volume relative to conventional techniques.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

The present invention provides an improved method for the extraction of hormones from a biological sample. Unlike prior art methods, the invention employs a digital microfluidic array for the transport of fluids during the extraction steps.

In a preferred embodiment, the present invention provides a method of extracting hormones from biological sample using a digital microfluidic array, where the biological sample may be blood, of blood, serum, plasma, urine or tissue. Advantageously, the invention does not rely on large sample volumes and detectable hormone levels may be efficiently extracted from sample volumes of 1 µL or lower.

Figure 1:
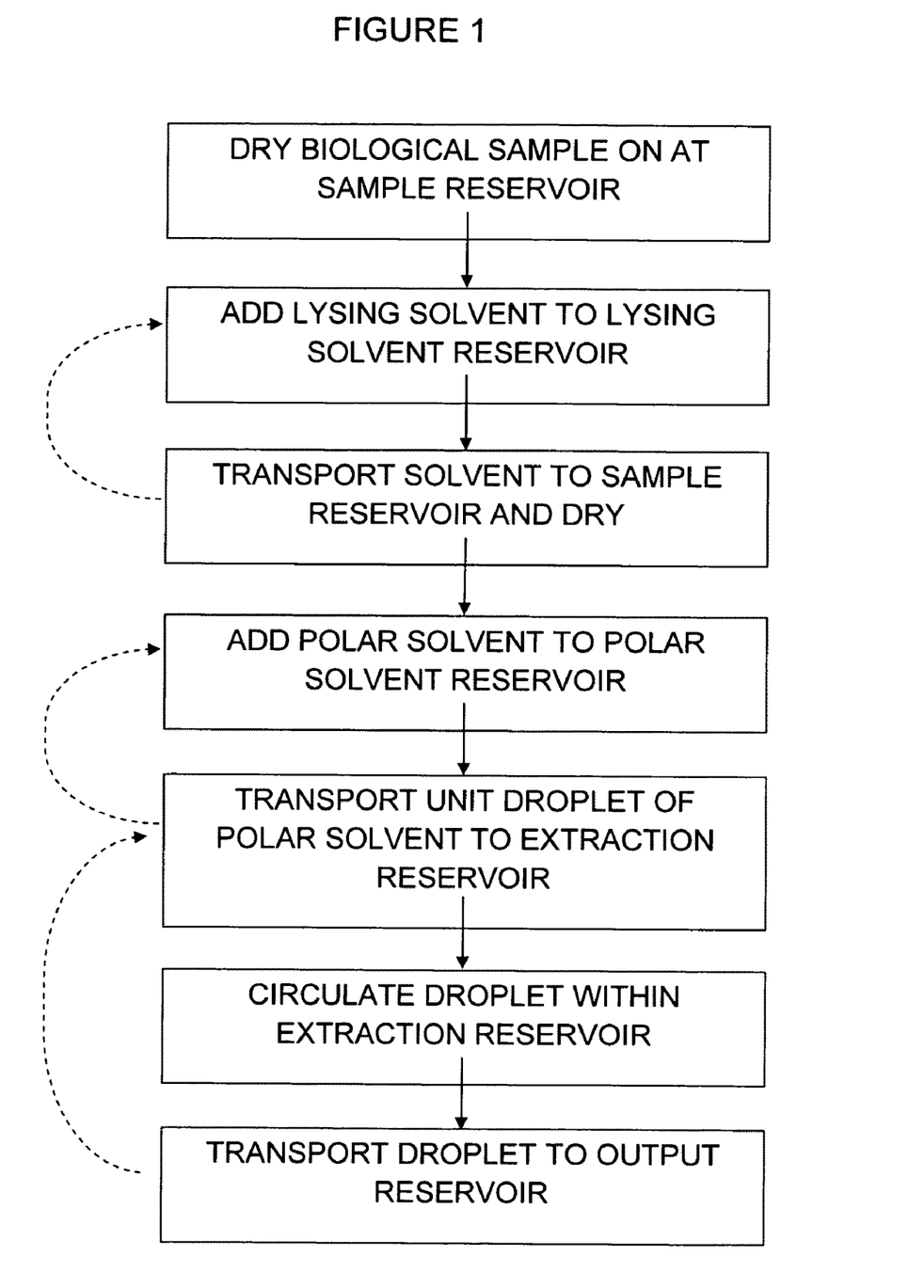
FIG. 1 shows a flow chart illustrating a preferred embodiment of the method according to the invention.

The main steps of the invention are provided in the flowchart shown in FIG. 1. The method is performed by drying and lysing a biological sample, extracting the hormones into a polar solvent, and purifying the solution of extracted hormone in polar solvent by moving droplets of the solution through a non-polar extraction solvent. Fluidic transport is achieved using a digital microfluidic array to move individual droplets of fluid between reservoirs.

One skilled in the art will readily appreciate that a digital microfluidic array comprises a planar surface, onto which an array of electrodes are deposited and subsequently coated with a hydrophobic insulator. The hydrophobic insulator is commonly Teflon-AF. Electrical contact pads are connected to the individual electrodes, enabling the electrodes to be individually addressed. The electrodes are arranged adjacent to each other in a plane to form a path over which fluid can be transported. The path may be one-dimensional or two-dimensional.

Sample and reagent reservoirs are typically incorporated into the array by including electrodes that are capable of supporting more than one unit droplet of fluid. Unit droplets can be extracted from reservoirs by actuating an electrode adjacent to the reservoir.

In a closed digital microfluidic array, a second planar surface, onto which a single planar electrode is typically deposited and subsequently coated with a layer of a hydrophobic insulator, is placed parallel to the first planar surface, forming a planar air gap. Fluid droplets placed on the array elements (i.e. on the insulating layer directly above an array electrode) can be made to move by applying a voltage between an array electrode and the single planar electrode. Alternatively, an open digital microfluidic array can be formed with the first surface alone, where droplets are moved by applying a voltage between neighbouring electrodes.

In one embodiment, the method of the invention is performed with a closed digital microfluidic array as described above. The electrodes are preferably square in shape with sides having a length of about 1 to 2 µm, and more preferably 1.5 µm. Accordingly, the array electrodes are preferably able to transport unit droplets with a volume in the range of about 200-400 nl. The spacing between electrodes is preferably in the range of about 20-60 µm, and more preferably about 40 µm. The gap between the upper and lower planes of the closed digital microfluidic array is preferably in the range of about 50-250 µm, and more preferably about 100 µm. However, the method of the invention can be performed with a wider range of droplet volume, for example, 10 picoliter to 3 mL. Likewise, the size and dimension of the electrode can vary depending on each application.

The array preferably includes a sample reservoir and one or more reagent reservoirs. The reservoirs preferably support a volume greater than one unit droplet. In one embodiment, the reservoir electrodes are sufficiently large to accommodate a volume of about 1 µL of fluid.

As shown in the first step of FIG. 1, sample is introduced to the microfluidic digital array and allowed to dry at the sample reservoir. As described above, the sample may be a liquid biological sample, or may be a tissue sample such as breast tissue. Preferably, the sample volume is in the microliter range, for example, 1-20 µL, and more preferably is about 1 µL, which is advantageously much lower than the sample volumes required by prior art sample preparation methods. Samples and reagents including solvents may be added to the array through multiple means, including the lateral opening between the two planar surfaces, or through access ports in the upper surface.

After the sample has dried, a lysing solvent is added to a reservoir on the array. The array is actuated by applying a voltage to transport the lysing solvent to the sample reservoir in order to lyse the dried sample. The array is preferably actuated so that lysing solvent is transported dropwise to the sample reservoir, until the lysing solvent at the lysing reservoir has been consumed. The lysing solvent is subsequently allowed to dry. In a preferred embodiment, this step of adding lysing solvent, transporting the lysing solvent to the sample reservoir, and drying the lysing solvent, is repeated one or more times to achieve efficient lysing of the sample (as indicated by the dashed arrow in FIG. 1).

Although many sample matrixes require lysing of cells, the extraction of hormones from certain matrices, such as urine, plasma and serum, may not require a lysing step. Accordingly, an embodiment of the present invention does not require the aforementioned lysing step for sample matrices that do not contain significant amounts of biological cells.

A volume of polar solvent is then added to a reservoir on the array. The reservoir may be a dedicated reservoir for the polar solvent, or may be the same reservoir as that used to dispense the lysing solvent in the preceding step of the method. The array is actuated to transport the polar solvent in a dropwise fashion to the sample reservoir. Once transported to the sample reservoir, the polar solvent solubilises the hormones present in the dried sample, forming a polar solution containing solubilised hormones.

The method further involves an extraction step in which contaminants are removed from the polar solution. This is achieved by passing droplets of the polar solution through a non-polar solvent. According to the present invention, the polar and non-polar solvents are chosen to ensure that a droplet of polar solvent may pass through a volume of non-polar solvent while maintaining its droplet phase, thereby enabling the extraction of contaminants into the non-polar solvent while maintaining a droplet form that can be addressed and transported by the digital microfluidic array. In a preferred embodiment, the non-polar solvent is added to the extraction reservoir subsequent to the preceding step of adding the polar solvent to the array. In another embodiment, the non-polar solvent is added to the extraction reservoir at substantially the same time that the polar solvent is added to the array.

In one embodiment of the invention. the lysing solvent can be a solution of about 80% dichloromethane and about 20% acetone by volume. Furthermore, the polar solvent can be methanol, and the non-polar solvent can be 2,2,4-Trimethylpentane (isooctane), or any solvent with dielectric point less than 15. However, the present invention is not limited to particular use of the solvents. Instead, the solvents and their volumes can vary depending on the analyte of interest and the type of biological sample analyzed.

To enable this element of the inventive method, the digital microfluidic array further includes an extraction reservoir comprising one or more electrodes. In a preferred embodiment, the extraction reservoir includes multiple electrodes. Also, the extraction reservoir preferably includes a wall to contain a volume of the non-polar solvent within the vicinity of the electrodes, where the wall does not interrupt the transport of liquid droplets into and out of the extraction reservoir. The wall need not form a contiguous boundary around the extraction reservoir, but should occupy a sufficient portion of a perimeter around the extraction reservoir to maintain the non-polar volume within the reservoir.

The extraction of contaminants from the polar solution is therefore accomplished by transporting a droplet of the polar solution from the sample reservoir to the extraction reservoir, where the presence of the non-polar solvent enables the extraction of contaminants from the droplet. Subsequently, the droplet is transported to an output reservoir by actuation of the array. In a preferred embodiment, the droplet is circulated within the extraction reservoir (by actuation of the array) one or more times to further assist in the removal of contaminants, before being transported to the output reservoir. In one embodiment, the electrodes within the extraction reservoir are arranged in a single row. In another embodiment, the electrodes are arranged in multiple rows. It should be noted, however, that the electrodes can be arranged in any design and shape depending on application. This process of extracting contaminants from the polar solution is preferably repeated until the polar solution residing at the sample reservoir has been substantially depleted, as shown by the dashed arrow in FIG. 1. In a preferred embodiment, the process steps from the addition of the polar solvent to the transfer of all polar solution to the output reservoir are repeated one or more times to obtain optimal extraction of hormones.

In an alternative embodiment of the method of the present invention, the method may be performed using an open microfluidic array. When performing the inventive method using an open microfluidic array, method steps should be performed sufficiently rapidly to enable the transport, mixing, extraction and solubilisation steps prior to the evaporation of reagents.

The hormones extracted from a biological sample according to the present preferably include sex steroids, and the sex steroids preferably include estrogen and testosterone. In a more preferred embodiment, the estrogen is estradiol.

The present invention also provides a method for the extraction and subsequent assaying of one or more hormones from a biological sample. The assay may be immunoassays such as ELISA, EIA, RIA, lateral flow and flow-through formats. Preferably, the assay method is mass spectroscopy, and more particularly is GC/MS, LC/MS, LC/MS/MS, MALDI-MS or MALDI-TOF.

In one embodiment, the extracted solution (after being transported to the output reservoir) may be dried, following which step an assay buffer prior may be added to solubilise the extracted hormones into a buffer that is preferable for performing an assay.

The assay may be used to measure the concentration of one or more hormones in the biological sample. The concentration of a given hormone in the biological sample can be obtained from the measured concentration of the hormone in the extracted solution (or assay buffer) by multiplying the concentration obtained from the assay by a factor equal to the ratio of a the volume of the extracted solution (or assay buffer) to the volume of biological sample.

The present invention will now be illustrated with the following non-limiting and exemplary example of extraction and detection of estrogen from µl samples, but it will be appreciated that this invention is not limited to estrogen or the solvents, solutions being used for estrogen extraction.

EXAMPLE

Extraction and Detection of Estrogen from µL Samples

Figure 2:
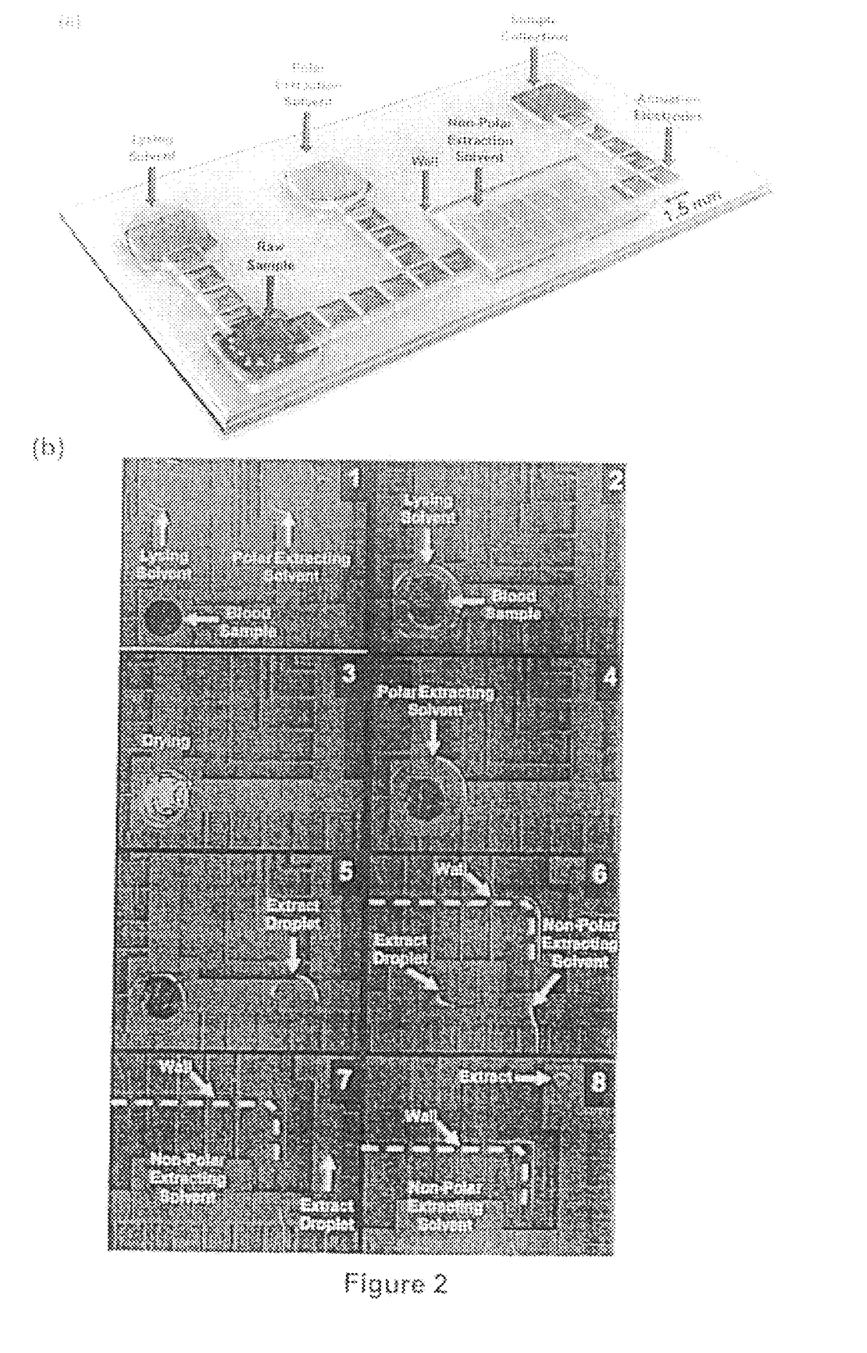
FIG. 2 shows a perspective view of a digital microfluidic (DMF) device design and operation, in which (a) shows a schematic of the DMF device, which includes sample and solvent reservoirs and the liquid-liquid extraction zone, and (b) a series of frames from a movie (1-8) illustrating the key steps in the DMF-based extraction of estrogen from a droplet of human blood (1 µL)

A digital microfluidic (DMF) device used for estrogen extraction is illustrated in FIG. 2a which shows a perspective view of a digital microfluidic (DMF) device design and operation, in which (a) shows a schematic of the DMF device, which includes sample and solvent reservoirs and the liquid-liquid extraction zone. FIG. 2(b) shows a series of frames from a movie (1-8) illustrating the key steps in the DMF-based extraction of estrogen from a droplet of human blood (1 µL). As shown, samples are lysed, the estradiol is extracted into a polar solvent (methanol), unwanted constituents are extracted into a non-polar solvent (isooctane), and the purified solution is delivered to a collection reservoir. Among the remarkable features of this technique is the ease with which the methanolic phase is separated from the isooctane phase after liquid-liquid extraction (as shown in frame 7).

Device Fabrication

The digital microfluidic devices as illustrated in FIG. 2(a) were fabricated in the University of Toronto Emerging Communications Technology Institute (ECTI) clean room facility, using transparency photomasks printed at City Graphics (Toronto, ON). Glass wafers (Howard Glass Co. Inc., Worcester, Mass.) were cleaned in piranha solution (10 min), and coated with chromium (150 nm) by electron beam deposition (BOC Edwards, Wilmington, Mass.). After rinsing (acetone, methanol, DI water) and baking on a hot plate (115° C., 5 min), substrates were primed by spin-coating HMDS (3000 rpm, 30 s) and then spin-coating Shipley S1811 photoresist (3000 rpm, 30 s). Substrates were baked on a hot plate (100° C., 2 min) and exposed (35.5 mW/cm2, 4 s) through a transparency photomask using a Karl Suss MA6 mask aligner (Garching, Germany). Then substrates were developed (MF321 developer, 3 min) and postbaked on a hot plate (100° C., 1 min). After photolithography, exposed chromium was etched (CR-4, 2 min) and the remaining photoresist was stripped by sonicating in AZ300T (5, min).

After forming electrodes and cleaning in piranha solution (30 s), a photoresist wall was formed, using methods similar to those reported by Moon et al. 20 Briefly, substrates were spin-coated with SU-8-25 (500 rpm, 5 s, then 1000 rpm, 30 s), baked on a hotplate (65° C., 5 min, then 95° C., 15 min), and then exposed to UV light (35.5 W/cm2, 7 s). After baking (65° C., 1 min, then 95° C., 4 min), and developing in SU-8 developer, substrates were coated with 2 µm of parylene-C and 100 nm of Teflon-AF. Parylene-C was applied using a vapor deposition instrument (Specialty Coating Systems, Indianapolis, Ind.) and Teflon-AF was spin-coated (1% by weight in Fluorinert FC-40, 1000 rpm, 1 min) followed by baking on a hot plate (160° C., 10 min). The polymer coatings were removed from contact pads by gentle scraping with a scalpel to facilitate electrical contact for droplet actuation. In addition to patterned devices, unpatterned indium-tin oxide (ITO) coated glass substrates (Delta Technologies Ltd, Stillwater, Minn.) were coated with Teflon-AF using the conditions described above.

The DMF device design of FIG. 2(a) included three input reservoir electrodes (3.5×3.5 mm) for the raw sample, lysing solvent, and polar extraction solvent, respectively, and a fourth reservoir electrode for collection of the processed sample. Actuation electrodes (1.5 mm×1.5 mm with a 40 µm inter-electrode gap) formed a path linking the input reservoirs, which passed through a fifth reservoir (delineated by a photoresist wall) containing non-polar extraction solvent. Devices were assembled with an unpatterned ITO-glass top plate and a patterned bottom plate separated by a spacer formed from one or two pieces of double-sided tape (90 or 180 µm thick). Thus, depending on the spacer thickness, reservoir volumes were ~1.1 or 2.2 µL, and unit droplets (covering a single actuation electrode) were ~200 or 400 mL. A single spacer was used to process standard solutions of estradiol, while a double spacer was used for blood, serum, and tissue. Droplets were sandwiched between the two plates and actuated by applying AC potentials (18 kHz, 100 V) between the top electrode (ground) and sequential electrodes on the bottom plate via the exposed contact pads. Droplet motion was monitored by a CCD camera mated to an imaging lens positioned over the top of the device.

Further details of DMF devices and methods of construction and use of detectors associated therewith are disclosed in copending U.S. patent application Ser. No. 12/285,020 filed Sep. 26, 2008, U.S. patent application Ser. No. 12/285,567 filed Oct. 8, 2008, and U.S. Provisional Patent Application Ser. No. 61/136,896 filed Oct. 10, 2008, all of which are incorporated herein by reference in their entirety. These US patent references show various DMF devices and methods of manufacture.

As shown, an array of separated electrodes which are independently activatable by a power supply, connects a series of reservoirs containing the sample and reagents. The process of estrogen extraction from a microliter of human blood is depicted in the movie frames of FIG. 2(b). As shown, in typical assays, samples were lysed, the estradiol was extracted into a polar solvent (methanol), unwanted constituents were extracted into a non-polar solvent (isooctane), and the purified solution was delivered to a collection reservoir. In addition to blood, the device and method illustrated in FIG. 2(a) was compatible with serum, breast tissue, and standard solutions, as described hereinafter.

Blood samples were collected from a healthy female volunteer on 5 different reproductive cycles (mid luteal phase). Serum was obtained by centrifugation of fresh blood samples at 800 RPM for 5 minutes, and both were kept at −20° C. until analysis. Breast tissue was obtained from apparently normal areas adjacent to breast cancer during surgery in two post-menopausal breast cancer patients and kept at −80° C. until analysis. Human ethics approvals were obtained from Mount Sinai Hospital and the Ontario Tumor Bank Research Ethics Boards (Toronto, Ontario, Canada).

Chemicals and Reagents

Dichloromethane (DCM) and 2,2,4-Trimethylpentane (Isooctane) 99.8% and HPLC-grade water were purchased from Sigma (Oakville, ON). Methyl alcohol (Methanol, HPLC grade) was from Fisher Scientific (Ottawa, ON). Estradiol (17-beta) was purchased from Steraloids Inc. (Newport, R.I.). Estradiol EIA ELISA kits were from ALPCO Diagnostics (Salem, N.H.). Shipley S1811 photoresist and MF321 developer from Rohm and Haas (Marlborough, Mass.), AZ300T photoresist stripper from AZ Electronic Materials (Somerville, N.J.), parylene C dimer from Specialty Coating Systems (Indianapolis, Ind.), Teflon-AF from DuPont (Wilmington, Del.), solid chromium from Kurt J. Lesker Canada (Toronto, ON), CR-4 chromium etchant from Cyantek (Fremont, Calif.), hexamethyldisilazane (HMDS) from Shin-Etsu MicroSi (Phoenix, Ariz.), concentrated sulfuric acid and hydrogen peroxide (30%) from Fisher Scientific Canada (Ottawa, ON), Fluorinert FC-40 from Sigma (Oakville, ON), and SU-8 and SU-8 developer from MicroChem (Newton, Mass.). Piranha solution was prepared as a 3/1 v/v mixture of sulfuric acid/hydrogen peroxide.

Methodology of Digital Microfluidic (DMF) Estrogen Extraction

Two DMF-driven estrogen extraction techniques were developed; Method I, used in most experiments, comprised four steps. First, an aliquot of whole blood, serum, breast tissue homogenate, or estradiol standard solution was positioned in the sample reservoir of a device. The sample can be added to the device by pipetting, microchannel based capillary suction, direct sample deposition, paper/tissue absorption and microneedle.

Standard solutions were used immediately, and blood, serum, or tissue homogenate samples were allowed to dry to the surface. The top plate was then affixed and the solvents (DCM/acetone 80:20 v/v as lysing solvent, methanol as polar extracting solvent, and isooctane as non-polar extracting solvent) were loaded. Second, a series of reservoir volumes (9×1.1 μL or 5×2.2 μL) of DCM/acetone was dispensed and driven by DMF drop-wise to the sample, each of which was allowed to incubate until dry (~1 min per reservoir volume).

Third, a reservoir volume of methanol (1.1 or 2.2 μL) was dispensed and driven by DMF to the dried lysate to dissolve the steroids. The dispensing can be carried out by, for example, pipetting.

It will be understood that the examples listed herein uses a limited list of solvents, but in general, depending on the extraction being undertaken, there is a broad spectrum of solvents, acids, alkalis and combination of solvents as well as solvent volumes that can be used according to the analyte of interest and the type of biological sample analyzed. Also, the arrangement of solvents in the reservoirs can be switched alternatively according to the polarity of the analyte of interest.

A unit droplet of the dissolved sample (200 or 400 nL) was dispensed and delivered by DMF to the isooctane reservoir and circulated within the pool (~20 s) prior to driving the droplet to the collection reservoir. This process was repeated until the sample reservoir was empty. Fourth, step three was repeated with successive reservoir volumes of methanol (for a total of 9×1.1 μL or 5×2.2 μL) to be sure to extract all of the free estradiol. Finally, all purified droplets were pooled in the output reservoir and allowed to dry.

In Method II, used to analyze percent recovery and experimental precision by ELISA, a standard solution of estradiol in methanol (1 μL) was positioned in the sample reservoir and the top plate was affixed (the lysis and polar solvent reservoirs remained empty). In each experiment, a single unit droplet (200 nL) of sample was dispensed, translated (and circulated) through isooctane, and delivered to the collection reservoir, all by DMF. The sample reservoir was then washed (manually) with methanol three times, and a fresh sample was positioned in the reservoir, and the process was repeated (twice), such that 3 purified droplets from replicate samples (i.e. ~600 mL total volume) were pooled in the collection reservoir and allowed to dry.

For all experiments, after collecting and drying the purified estrogenic solution, devices were stored at −20° C. Immediately prior to analysis, each extract was resolubilized in an aliquot (30 μL) of methanol/DCM (2:1 v/v), which was then dispensed into a small centrifuge tube. The solvent was then evaporated and the dry extract was reconstituted in a medium specific for the desired analysis.

Detection by Mass Spectrometry

Mass spectrometry was used to evaluate the performance of the DMF clean-up process in samples of whole blood or serum (obtained at two different days of the reproductive cycle). In each experiment, a 5 μL sample was dried and extracted by DMF (method one, as above), and the extract was reconstituted in 50 μL of methanol containing formic acid (0.1% v/v). Control (non-extracted) samples were prepared by drying and reconstituting 5-μL aliquots of blood or serum in 50 μL of methanol/formic acid (0.1% v/v), sonicating (10 min), and passing through a syringe filter (nylon membrane, 0.2 μm pore dia.). Samples were injected by nano-electrospray into an LTQ Mass Spectrometer (Thermo Scientific, Waltman, Mass.) operating in the negative mode at 250° C. with a flow rate of 0.5 μL/min. Replicate spectra were obtained for DMF-extracted and control samples of both blood and serum.

Liquid chromatography and tandem mass spectrometry (LC-MS/MS) with multiple reaction monitoring (MRM) was used to evaluate estradiol in extracts from standard solutions, as well as in whole blood and breast tissue samples. Standard solutions (1 μL, 2 mg/mL in methanol) and blood (dried from 1 μL) were extracted by DMF (method one, as above) with no prior processing, while breast tissue (400 mg) was manually homogenized in DCM (1 mL), from which 1 μL samples were dried and processed similarly. In all cases, after extraction, samples were resuspended in 100 µL of methanol:water (20:80 v/v) and injected onto an HPLC (HP-Agilent 1100 series LC) interfaced by electrospray to a QTRAP LC-MS/MS (Applied Biosystems, Foster City, Calif.). The samples were analyzed in negative mode with multiple reaction monitoring, evaluating m/z 271 and 145 as an estradiol ion pair 21 to determine the extracted-ion current (XIC). Operating parameters included 0.300 µL/min flow rate, 4200 V spray potential, 60 collision energy and 400° C. temperature.

Detection by ELISA

An estradiol-specific ELISA was used (a) to evaluate the recovery and precision of the DMF method, and (b) to quantify estradiol in breast tissue samples. In these experiments, at least 3 replicate samples were evaluated for each condition by absorbance, measured at 450 nm using a µQuant microplate spectrophotometer (Bio-Tek, Instruments, Winooski, Vt.). The optical densities of samples and controls were compared with those of ELISA calibrator solutions using a standard curve to calculate estradiol concentrations as per the manufacturer's instructions.

For application (a), analysis of recovery and precision, the samples comprised serial dilutions of estradiol standard (500, 250, 100, and 3.3 ng/mL) in methanol. DMF-extracts of 3×1 µL samples were prepared using method two (as above), and for comparison, (non-extracted) control samples were prepared using the same procedure, but in devices lacking isooctane. After extraction, samples were resuspended in a 50-µL mixture of deesterified serum (ALPCO Diagnostics) and methanol (4:1 v/v) and evaluated by ELISA. Recovery percentages were calculated as the inverse of the optical densities from extracted samples divided by those from non-extracted controls. For application (b), 1-µL samples of breast tissue homogenate (200 mg) in DCM (0.5 ml) from a breast cancer patient (a different patient than the one evaluated by MS) were processed manually (as above) and extracted by DMF using method one. The extractate was reconstituted in a 50-µL mixture of deesterified serum/methanol mixture (4:1 v/v) and was evaluated by ELISA.

Results

Figure 3:
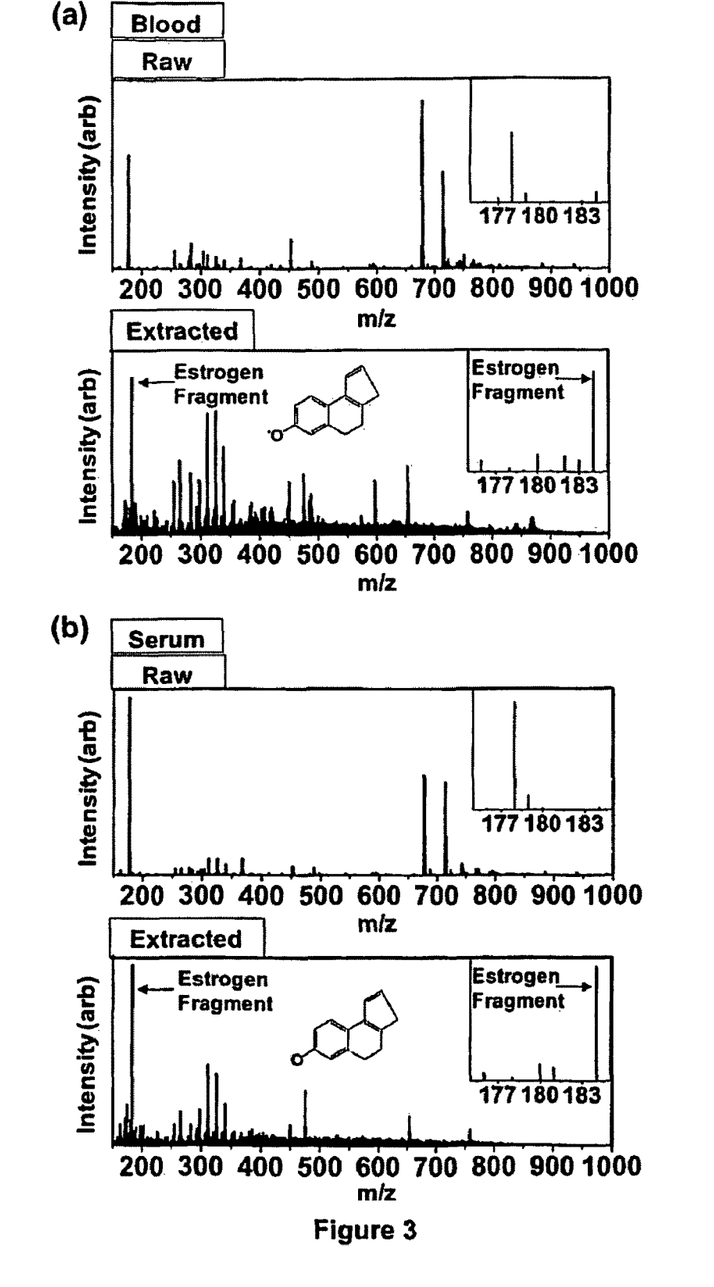
FIG. 3 shows mass spectra of raw and DMF-extracted samples, representative spectra generated from (a) blood and (b) serum obtained from a female volunteer at different days of the menstrual cycle in which the insets show that the estrogen fragment at m/z 183 is detected in extracted samples but not in raw samples.

As mentioned above, mass spectrometry was used to evaluate the efficacy of extraction by the digital microfluidic method. FIG. 3 contains representative spectra generated from raw samples and extracted samples of blood and serum obtained from a female volunteer at two different days of one reproductive cycle. Specifically, FIGS. 3(a) and (b) show the mass spectra of raw and DMF-extracted samples. Representative spectra generated from 2(a) blood and 2(b) serum obtained from a female volunteer at different days of the menstrual cycle. The insets show that the estrogen fragment at m/z 183 is detected in extracted samples but not in raw samples. In addition, several peaks of potential interferants, tentatively identified as fragments of tyrosine (m/z 178) DNA helicase (m/z 677), and porphyrin (m/z 715) are absent in the extracted samples, suggesting that their concentrations have been substantially reduced.

As shown, estradiol (m/z 183) was not detected in the spectra of raw samples, but was the peak of highest intensity in those from DMF-extracted samples. In addition, the intensities of peaks of potential interferants, tentatively identified as fragments of tyrosine [22] (m/z 178), DNA helicase (http://gpmdb.rockefeller.edu/) (m/z 677) [23] and porphyrin [24] (m/z 715), were suppressed in the spectra of extracted samples, indicating that their concentrations had been substantially reduced. These data highlight the importance of sample processing for this application—estradiol can only be ionized (and thus detected by mass spectrometry) after the many interfering compounds are removed [25].

Figure 4:
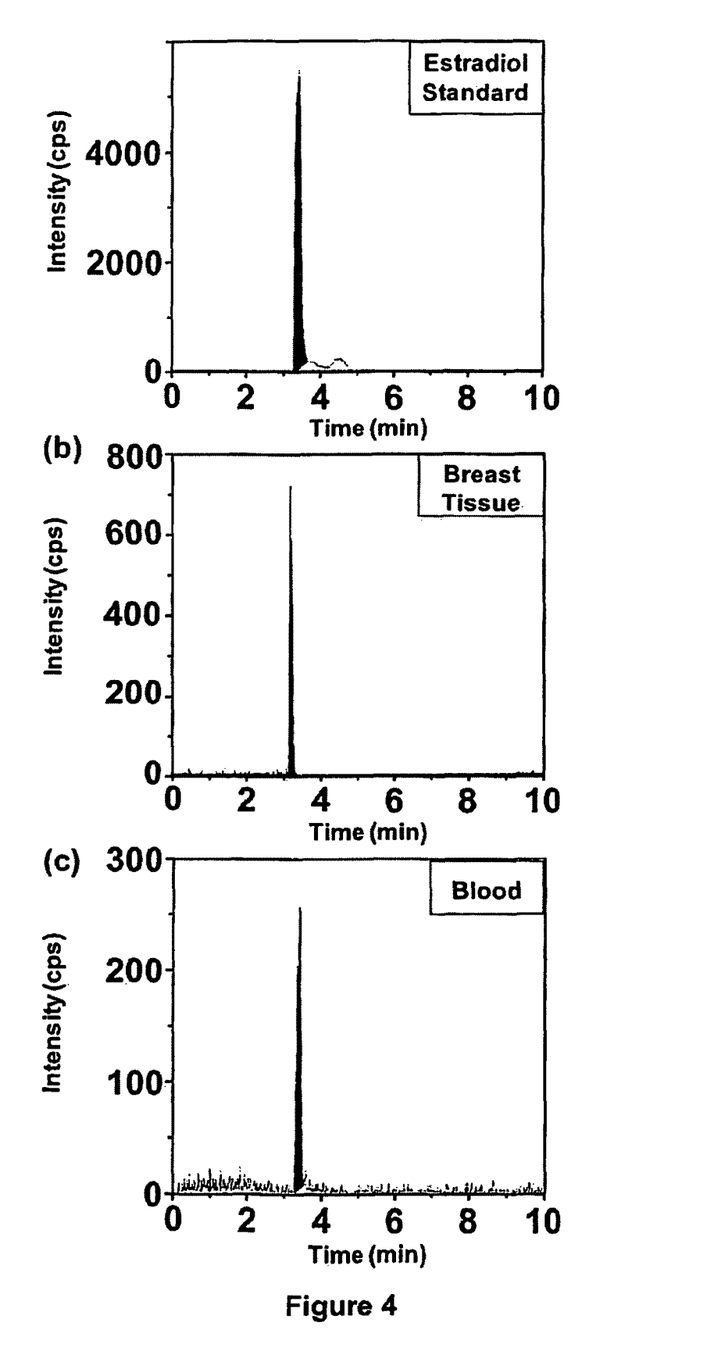
FIG. 4 shows LC-MS/MS analysis of DMF-extracted samples showing extracted-ion current (XIC) chromatograms generated by LC-MS/MS with multiple reaction monitoring from µL samples of (a) estradiol standard solution (2 mg/mL), (b) breast tissue of a postmenopausal patient with breast cancer, and (c) whole blood. The estradiol-specific ion pair evaluated for XIC was m/z 271/145.

FIGS. 4(a) to (c) show the LC-MS/MS analysis of DMF-extracted samples. Extracted-ion current (XIC) chromatograms generated by LC-MS/MS with multiple reaction monitoring from µL samples of estradiol standard solution (2 mg/mL) (see FIG. 4(a)), breast tissue of a postmenopausal patient with breast cancer (see FIG. 4(b)), and whole blood (see FIG. 4(c)). The estradiol-specific ion pair evaluated for XIC was m/z 271/145. More specifically, to test the limits of the method disclosed herein for detecting estrogen in small samples, liquid chromatography and tandem mass spectrometry (LC-MS/MS) with multiple reaction monitoring (MRM) was used to evaluate estradiol extracted by DMF from standard solutions (FIG. 4(a)), breast tissue homogenate from a postmenopausal breast cancer patient (FIG. 4(b)) and whole blood from a female volunteer (FIG. 4(c)). As shown, estradiol was detected with high signal-to-noise ratio (S/N) at retention time ~3.2 min for all cases. Detection with high S/N in such tiny samples (1 µL) suggests that in the future, the new technique may be useful for non-invasive sex steroid testing.

Figure 5:
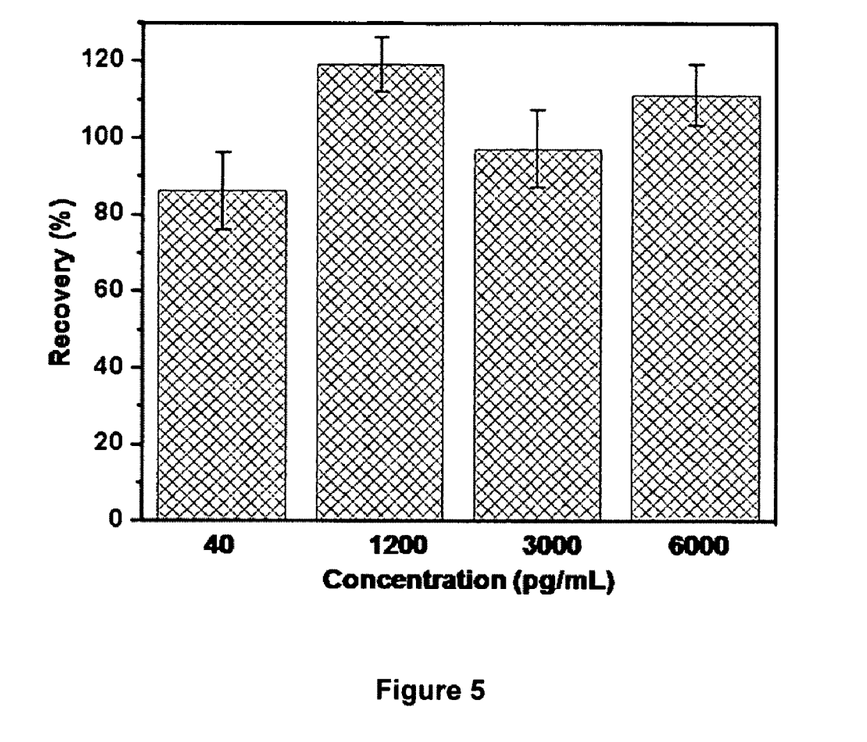
FIG. 5 shows plots of Recovery (%) versus concentration showing extraction efficiency analysis by ELISA, in which estradiol standards before and after extraction were evaluated by ELISA.

An absorbance-based ELISA was used to evaluate the compatibility of the new method with standard optical detection techniques. First, a method was developed for analyzing estradiol standards in a range of concentrations. FIG. 5 shows the extraction efficiency analysis by ELISA. Estradiol standards before and after extraction were evaluated by ELISA. As shown, extraction efficiencies from standard solutions (500, 250, 100, and 3.3 ng/mL) ranged from 86 to 119% with a CVs ranging from 7 to 10%. As shown in FIG. 5, the DMF-based extraction efficiencies were high, ranging from 86 to 119% with CVs ranging from 7-10%. A similar method was then applied to analyzing extracts from breast tissue homogenate from a postmenopausal breast cancer patient. Replicate analyses of 1 µL samples (requiring ~20 min ea.) contained a mean concentration of 807 µg/mL estradiol. These data confirm that the new method disclosed herein is capable of robust, quantitative analyses of tiny volumes of clinically relevant samples.

Figure 6:
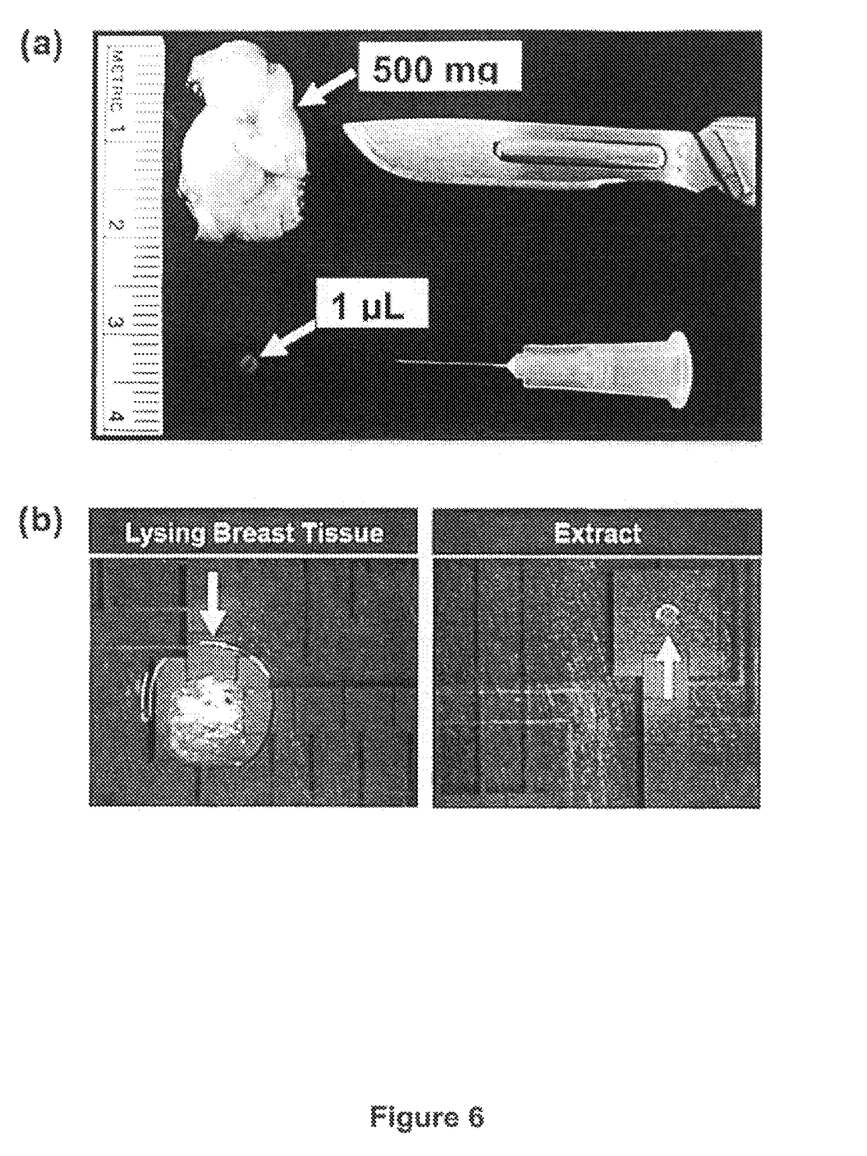
FIG. 6 (a) is a picture of 500 mg of breast tissue collected by incisional biopsy (representing the sample size required for conventional analysis methods) compared to a 1 µL microaspirate collected using a 30 ga. needle (representing the sample size used with the new method), and (b) shows pictures of breast tissue microaspirate (1 µL) being lysed on the DMF device and of the dried estrogen extracted from it.

To the best of the inventors' knowledge, this is the first disclosure of a method for the extraction of steroids, hormones, sex hormones from microliter-sized clinical samples. These volumes are 500 times less smaller than those required for conventional analysis methods [16, 17, 26-28]. FIG. 6(a) shows a picture of 500 mg of breast tissue collected by incisional biopsy (representing the sample size required for conventional analysis methods) compared to a 1 µL microaspirate collected using a 30 ga. needle (representing the sample size used with the new method). FIG. 6(b) shows pictures of breast tissue microaspirate (1 µL) being lysed on the DMF device and of the dried estrogen extracted from it.

As depicted in FIGS. 6(a) and (b), this substantial reduction in sample size may eventually result in drastically less-invasive collection procedures, facilitating routine testing of finger pricks of blood or microaspirates of tissue. The former (finger pricks) would facilitate improved patient compliance and clinical outcomes for a variety of applications related to women's health—for example, infertility patients could be monitored over the span of their menstrual or assisted-reproduction cycles, which would assist in proper timing of clinical interventions. The latter (tissue microaspirates) could have an even greater impact on women's health, as described below.

The new method reported here allows for the analysis of estrogen in tiny samples of homogenized breast tissue from menopausal breast cancer patients. It is now widely accepted that estrogen is a significant intracrine and paracrine factor (as opposed to a circulatory hormone) in many tissues including the breast [29-31]. Indeed, in situ biosynthesis of estrogen contributes up to 75% of the total estrogen produced in pre-menopausal women and almost 100% in menopausal women [29]. Thus, blood estrogen is not reflective of local concentrations inside the breast and may not be sufficient for identification of women with high risk for developing breast cancer, or to monitor the effect of anti-estrogen breast cancer therapies [32, 33]. While this is widely recognized, the measurement of local concentrations of estrogens is not common, because of the present requirement for a large tissue biopsy (which requires local anesthesia and carries the risk of scarring or deformity). Thus, the inventors believe that the digital microfluidic method reported here, which does not require large tissue biopsies (and is compatible with non-scarring, low-invasive microaspirate samples), has the potential to ushering in a new era of treatment and diagnosis of breast cancer relying on routine measurement of local tissue concentrations of estrogen.

In addition to the advantages that come with smaller samples, the automation and integration in the digital microfluidic method makes it considerably less time- and labor-intensive relative to conventional techniques (e.g., no centrifuge is used and the pipetting and prolonged drying steps are almost eliminated). In its current form, samples were processed on DMF devices and then transferred to a more conventional format for analysis by mass spectrometry or ELISA. The former method (MS) is particularly attractive for laboratory testing; we are currently developing comprehensive LC-MS/MS methods for simultaneous quantification of a number of sex steroid hormones from a single sample. The latter method (ELISA) is attractive for point-of-care applications; we envision future devices and methods with on-chip estrogen quantitation, suitable for use in the clinic.

A feature of the current work is integrated sample extraction and cleanup. These steps are needed for tissue samples, but for serum samples, there are several so-called "direct" immunoassay kits intended for use in raw (non-extracted) samples. Unfortunately, these tests have been characterized as being non-specific and inaccurate because of cross reactivity with other hormones, and consensus is building that sample clean-up is a prerequisite for accurate evaluation of human serum estrogens [10, 13, 34, 35] and other steroids. In fact, the CDC has stated publicly that direct immunoassays do not generate reliable results, especially for samples containing low concentrations of steroids [36]. Thus, we anticipate that integrated sample cleanup methods like the one described here may prove useful for a wide range of clinically relevant applications.

The methods described herein are powered by digital microfluidics, a technology that has received less attention than the related technique of microchannel-based fluidics. While microchannels are well suited for many applications (e.g., electrophoresis and other separation modalities, in vitro culture and analysis of cells, etc.), we posit that this format is a poor match for the application reported here. Indeed, in the few reports [37-39] of microchannel-powered methods for liquid-liquid extraction (representing only one of a series of steps required for estrogen extraction from clinical samples) the techniques have been inherently limited by the challenge of separating and collecting one phase from the other after they have come into contact. In contrast, this process is straightforward in the method reported here (FIG. 1b, frame 7), and the precise control over different reagents [40], phases [41] and volumes [42] afforded by digital microfluidics makes it a near-perfect match for this application.

In summary, the foregoing example has disclosed a lab-on-a-chip powered by digital microfluidics for sample clean-up and extraction of estradiol in microliter-sized clinical samples. This method has significant potential for clinical applications in reproductive endocrinology and breast cancer.

The examples and embodiments described herein are for illustrative purposes only. Modifications or changes in light thereof will be suggested to persons skilled in the art and are to be included within the spirit and purview of this application.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention.

As used herein, the terms "about", and "approximately" when used in conjunction with ranges of concentrations, temperatures or other physical or chemical properties or characteristics is meant to cover slight variations that may exist in the upper and lower limits of the ranges of properties/characteristics.

Also, as used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

References

1. Ehrmann, D. A. Polycystic ovary syndrome. New England Journal of Medicine 352 (2005).
2. Smith, S., Pfeifer, S. M. & Collins, J. A. Diagnosis and Management of Female Infertility. Journal of the American Medical Association 290, 1767-1770 (2003).
3. Henderson, B. E., Ross, R. & Bernstein, L. Estrogens as a cause of human cancer: the Richard and Hinda Rosenthal Foundation award lecture. Cancer Res 48, 246-253 (1988).
4. Kaaks, R. et al. Postmenopausal serum androgens, oestrogens and breast cancer risk: The European prospective investigation into cancer and nutrition. Endocrine-Related Cancer 12, 1071-1082 (2005).
5. Pitt, F. A. & Brazier, J. Hormone replacement therapy for osteoporosis. Lancet 335, 978 (1990).
6. Szarewski, A. & Guillebaud, J. Contraception. Current state of the art. British Medical Journal 302, 1224-1226 (1991).
7. Djerassi, C. Chemical birth of the pill. American Journal of Obstetrics and Gynecology 194, 290-298 (2006).
8. Hertz, R. & Bailar 3rd, J. C. Estrogen-progestogen combinations for contraception. Journal of the American Medical Association 198, 1000-1006 (1966).
9. Cunningham, G. R. Testosterone replacement therapy for late-onset hypogonadism. Nature Clinical Practice Urology 3, 260-267 (2006).
10. Stanczyk, F. Z., Lee, J. S. & Santen, R. J. Standardization of Steroid Hormone Assays Why, How, and When? Cancer Epidemiol Biomarkers Prev 16, 1713-1719 (2007).

11. Albrecht, L. & Styne, D. Laboratory testing of gonadal steroids in children. Pediatric Endocrinology Reviews 5, 599-607 (2007).
12. Rahhal, S. N., Fuqua, J. S. & Lee, P. A. The impact of assay sensitivity in the assessment of diseases and disorders in children. Steroids 73, 1322-1327 (2008).
13. Ankarberg-Lindgren, C. & Norjavaara, E. A purification step prior to commercial sensitive immunoassay is necessary to achieve clinical usefulness when quantifying serum 17-estradiol in prepubertal children. Eur J Endocrinol 158, 117-124 (2008).
14. Belanger, C. et al. Omental and subcutaneous adipose tissue steroid levels in obese men. Steroids 71, 674-682 (2006).
15. Labrie, F. et al. Androgen glucuronides, instead of testosterone, as the new markers of androgenic activity in women. The Journal of Steroid Biochemistry and Molecular Biology 99, 182-188 (2006).
16. Szymczak, J., Milewicz, A., Thijssen, J. H. H., Blankenstein, M. A. & Daroszewski, J. Concentration of Sex Steroids in Adipose Tissue after Menopause. Steroids 63, 319-321 (1998).
17. Blankenstein, M. A. et al. Intratumoral levels of estrogens in breast cancer. J Steroid Biochem Mol Biol 69, 293-297 (1999).
18. Santen, R. J. et al. Superiority of gas chromatography/tandem mass spectrometry assay (GCIMS/MS) for estradiol for monitoring of aromatase inhibitor therapy. Steroids 72, 666-671 (2007).
19. Wheeler, A. R. CHEMISTRY: Putting Electrowetting to Work. Science 322, 539-540 (2008).
20. Moon, H., Wheeler, A. R., Garrell, R. L., Loo, J. A. & Kim, C. J. An integrated digital microfluidic chip for multiplexed proteomic sample preparation and analysis by MALDI-MS. Lab Chip 6, 1213-1219 (2006).
21. Gentili, A. et al. Analysis of free estrogens and their conjugates in sewage and river waters by solid-phase extraction then liquid chromatography-electrospray-tandem mass spectrometry. Chromatographia 56, 25-32 (2002).
22. Deng, C., Li, W. & Zhang, X. Rapid determination of amino acids in neonatal blood samples based on derivatization with isobutyl chloroformate followed by solid-phase microextraction and gas chromatography/mass spectrometry. Rapid Communications in Mass Spectrometry 18, 2558-2564 (2004).
23. Macromolecules, N.R.f.M.S.A.o.B. & University, a.R. 2009).
24. Danton, M. & Lim, C. K. Porphyrin profiles in blood, urine and faeces by HPLC/electrospray ionization tandem mass spectrometry. Biomedical Chromatography 20, 612-621 (2006).
25. Jessome, L. L. & Volmer, D. A. Ion Suppression: A Major Concern in Mass Spectrometry. LC-GC North America 24, 498-510 (2006).
26. Chetrite, G. S., Cortes-Prieto, J. C., Philippe, J. C. & Pasqualini, J. R. Estradiol inhibits the estrone sulfatase activity in normal and cancerous human breast tissues. Journal of Steroid Biochemistry and Molecular Biology 104, 289-292 (2007).
27. Burstein, H. J. Aromatase inhibitor-associated arthralgia syndrome. Breast 16, 223-234 (2007).
28. Falk, R. T. et al. Measurement of Sex Steroid Hormones in Breast Adipocytes: Methods and Implications. Cancer Epidemiol Biomarkers Prev 17, 1891-1895 (2008).
29. Labrie, F. Intracrinology. Molecular and Cellular Endocrinology 78, C113-C118 (1991).
30. Sasano, H., Suzuki, T. & Harada, N. From Endocrinology to Intracrinology. Endocr Pathol 9, 9-20 (1998).
31. Simpson, E. R. et al. Estrogen—the Good, the Bad, and the Unexpected. Endocr Rev 26, 322-330 (2005).
32. Lamar, C. A. et al. Serum sex hormones and breast cancer risk factors in postmenopausal women. Cancer Epidemiol Biomarkers Prev 12, 380-383 (2003).
33. Beattie, M. S. et al. Endogenous sex hormones, breast cancer risk, and tamoxifen response: an ancillary study in the NSABP Breast Cancer Prevention Trial (P-1). J Natl Cancer Inst 98, 110-115 (2006).
34. Dibbelt, L., Von Postel, G. & Knuppen, R. Determination of natural and synthetic estrogens by radioimmunoassay (I). Comparison of direct and extraction methods for quantification of estrone in human serum. Clinical Laboratory 44, 137-143 (1998).
35. Diver, M. J. & Nisbet, J. A. Warning on plasma oestradiol measurement. Lancet 2, 1097 (1987).
36. Cuzick, J. Chemoprevention of breast cancer. Women's Health 2, 853-861 (2006).
37. Kralj, J. G., Sahoo, H. R. & Jensen, K. F. Integrated continuous microfluidic liquid-liquid extraction. Lab on a Chip—Miniaturisation for Chemistry and Biology 7, 256-263 (2007).
38. Okubo, Y. et al. Liquid-liquid extraction for efficient synthesis and separation by utilizing micro spaces. Chemical Engineering Science 63, 4070-4077 (2008).
39; Znidarsic-Plazl, P. & Plazl, I. Steroid extraction in a microchannel system—mathematical modelling and experiments. Lab Chip 7, 883-889 (2007).
40. Chatterjee, D., Hetayothin, B., Wheeler, A. R., King, D. J. & Garrell, R. L. Droplet-based microfluidics with non-aqueous solvents and solutions. Lab Chip 6, 199-206 (2006).
41. Jebrail, M. J. & Wheeler, A. R. Digital microfluidic method for protein extraction by precipitation. Anal Chem 81, 330-335 (2009).
42. Abdelgawad, M., Freire, S. L. S., Yang, H. & Wheeler, A. R. All-terrain droplet actuation. Lab on a Chip—Miniaturisation for Chemistry and Biology 8, 672-677 (2008).

Therefore what is claimed is:

1. A method of extracting one or more hormones from a volume of biological sample using a digital microfluidic electrode array, including the steps of:

(a) drying said biological sample at a sample reservoir addressable by said electrode array;

(b) adding a volume of lysing solvent to a lysing reservoir addressable by said electrode array and actuating said electrode array to transport said volume of lysing solvent to said sample reservoir, and drying said lysing solvent at said sample reservoir;

(c) adding a volume of polar solvent to a polar solvent reservoir addressable by said array and actuating said electrode array to transport said volume of polar solvent to said sample reservoir, thereby obtaining a solution in which said one or more hormones are dissolved;

(d) actuating said electrode array to transport a droplet of said solution from said sample reservoir to an extraction reservoir containing a volume of non-polar solvent, said non-polar solvent chosen to extract contaminants from said droplet of said solution while maintaining said droplet of said solution as a distinct liquid phase that can be transported by said electrode array relative to said non-polar solvent;

(e) actuating said electrode array to transport said droplet of said solution from said extraction reservoir to an output reservoir; and (f) repeating steps (d) and (e) until said solution has been substantially removed from said sample reservoir, thereby obtaining a volume of purified solution located at said output reservoir.

2. The method according to claim 1 wherein step (b) is repeated one or more times.

3. The method according to claim 2 wherein steps (c)-(f) are repeated one or more times.

4. The method according to claim 1 wherein steps (c)-(f) are repeated one or more times.

5. The method according to claim 1 whereby said non-polar solvent is localized within said extraction reservoir by a wall means, where said wall means does not interrupt the path of a droplet as it is transported to and from said extraction reservoir.

6. The method according to claim 1 wherein said extraction reservoir spatially overlaps with multiple electrodes of said digital microfluidic array.

7. The method according to claim 6 wherein said droplet of solution is circulated within said extraction reservoir one or more times prior to step (e) by actuating said multiple electrodes.

8. The method according to claim 6 wherein said multiple electrodes are arranged in a single row.

9. The method according to claim 6 wherein said multiple electrodes are arranged in multiple adjacent rows.

10. The method according to claim 1 wherein said one or more hormones are lipid hormones, steroidal hormones, sterol hormones, prostaglandins, amine derived hormones, peptide or protein hormones.

11. The method according to claim 10 wherein said one or more steroids are selected from the group consisting of estrogens, androgens, progestins progestogens, glucocorticoids and mineralocorticoids .

12. The method according to claim 11 where said estrogen is estradiol, estrone, estriol, estrogen metabolites, phytoestrogens, synthetic estrogens, equilin, equilenin, ethinyl estradiol, and bio-identical estrogens.

13. The method according to claim 1 wherein said biological sample is selected from the group consisting of blood, serum, plasma, follicular fluid, endometrial fluid, pelvic fluid, semen, urine, cerebrospinal fluid, and tissue.

14. The method according to claim 13 wherein said tissue is breast tissue, endometrial tissue, ovarian tissue, vaginal tissue, testicular tissue, prostate tissue, adipose tissue, brain tissue, liver tissue, hair or skin.

15. The method according to claim 1 wherein a volume of said biological sample is about 1 to about 20 µL.

16. The method according to claim 1 wherein said sample is added to said digital microfluidic array by pipetting, microchannel based capillary suction, direct sample deposition, paper/tissue absorption or microneedle.

17. The method according to claim 1 wherein said lysing solvent, polar solvent and non-polar solvent are added to said digital microfluidic array by pipetting.

18. The method according to claim 7 wherein said lysing solvent is a solution of about 80% dichloromethane and about 20% acetone by volume.

19. The method according to claim 12 wherein said polar solvent is methanol.

20. The method according to claim 12 wherein said non-polar solvent is 2,2,4-Trimethylpentane (isooctane) or a solvent with dielectric point less than 15.

21. The method according to claim 1 wherein said droplet volume is in the range of between about 10 picoliter to about 3 mL.

22. The method according to claim 1 wherein said volume of lysing solvent added to said lysing solvent reservoir is about 1 µL.

23. The method according to claim 1 wherein said volume of polar solvent added to said polar solvent reservoir is about 1 µL.

24. The method according to claim 1 wherein said lysing reservoir and said polar solvent reservoir are a single reservoir.

25. The method according to claim 1 wherein said digital microfluidic array comprises substantially square electrodes having sides with a length in the range of about 1 to about 2 mm.

26. The method according to claim 25 wherein said digital microfluidic array comprises substantially square electrodes having sides with a length of about 1.5 mm.

27. The method according to claim 25 wherein an inter-electrode spacing between said electrodes, within the plane of said electrodes, is in the range of about 20-60 µm.

28. The method according to claim 25 wherein an inter-electrode spacing between said electrodes, within the plane of said electrodes, is about 40 µm.

29. The method according to claim 1 wherein said digital microfluidic array is a closed platform whereby fluid droplets are sandwiched between two planar surfaces and said array is actuated by applying a voltage between electrodes on each of said two planar surfaces.

30. The method according to claim 1 wherein a spacing between an upper and lower plate bounding fluids actuated by said digital microfluidic array is in the range of about 50-250 µm.

31. The method according to claim 29 wherein a spacing between an upper and lower plate bounding fluids for actuation by said digital microfluidic array is about 100 µm.

32. The method according to claim 1 wherein said digital microfluidic array is an open digital array comprising a single planar surface and said array is actuated by applying a voltage between two electrodes within said planar surface.

33. The method according to claim 1 wherein said purified solution is subsequently analyzed by an assay.

34. The method according to claim 33 wherein said assay is an immunoassay format selected from the group consisting of ELISA (enzyme-linked immunosorbent assay), EIA (enzyme immunoassay), RIA (radioimmunoassay), lateral flow and flow-through, and Magnetic Immunoassay.

35. The method according to claim 33 wherein said assay is a mass spectroscopy format selected from the group consisting of GC/MS (gas chromatography/mass spectrometry), LC/MS (liquid chromatography/mass spectrometry), LC/MS/MS (liquid chromatography/ mass spectrometry/ mass spectrometry), MALDI-MS (matrix assisted laser desorption ionization-mass spectrometry) and MALDI-TOF (matrix assisted laser desorption ionization-time of flight), DESI-MS (droplet electrospray ionization-mass spectrometry) and IMS/MS (ion mobility spectrometry/mass spectrometry).

36. The method according to claim 33 wherein said volume of purified solution is dried and said one or more hormones are solubilised in an assay buffer, solvent prior to performing said assay or direct on-chip detection assay.

37. The method according to claim 33 including detecting for said one or more hormones in said volume of purified solution with said purified volume on a pre-selected location on said electrode array in a field of view of an on-chip detection means, or after said purified volume has been removed from said electrode array.

38. The method according to claim 1 including a separate reservoir for each solvent and/or liquid used in said extraction, each separate reservoir being in flow communication with said electrode array.

39. The method according to claim 1 including constructing the digital microfluidic electrode array in which a size and spacing of electrodes in said electrode array are selected according to the extraction process being carried out.

40. A method for measuring the concentration of one or more hormones from a biological sample, comprising the steps of:
 (a) purifying said sample according to the method of claim 1;
 (b) performing an assay to measure a concentration of said one or more hormones in said purified solution; and
 (c) obtaining a concentration of said one or more hormones in said biological sample by multiplying said concentration of said one or more hormones in said purified solution by a suitable correction factor.

41. The method according to claim 40 wherein said suitable correction factor is the ratio of a said volume of purified solution to said volume of biological sample.

42. A method for measuring the concentration of one or more hormones from a biological sample, comprising the steps of:
 (a) purifying said sample according to the method of claim 1;
 (b) drying said volume of purified sample and solubilising said one or more hormones in an assay buffer;
 (b) performing an assay to measure a concentration of said one or more hormones in said assay buffer; and
 (c) obtaining a concentration of said one or more hormones in said biological sample by multiplying said concentration of said one or more hormones in said purified solution by a suitable correction factor.

43. The method according to claim 42 wherein said suitable correction factor is the ratio of a said volume of assay buffer to said volume of biological sample.

\* \* \* \* \*